(12) United States Patent
Mestha et al.

(10) Patent No.: US 7,333,208 B2
(45) Date of Patent: Feb. 19, 2008

(54) FULL WIDTH ARRAY MECHANICALLY TUNABLE SPECTROPHOTOMETER

(75) Inventors: Lalit Keshav Mestha, Fairport, NY (US); Yao Rong Wang, Webster, NY (US); Joel A. Kubby, Rochester, NY (US)

(73) Assignee: Xerox Corporation, Norwalk, CT (US)

( * ) Notice: Subject to any disclaimer, the term of this patent is extended or adjusted under 35 U.S.C. 154(b) by 281 days.

(21) Appl. No.: 11/016,952

(22) Filed: Dec. 20, 2004

(65) Prior Publication Data

US 2006/0132787 A1    Jun. 22, 2006

(51) Int. Cl.
*G01J 3/45* (2006.01)
*G01B 11/02* (2006.01)
*G01B 9/02* (2006.01)

(52) U.S. Cl. ........................ 356/454; 356/497
(58) Field of Classification Search ................ 356/454, 356/451, 519, 456, 479, 497, 480; 347/19
See application file for complete search history.

(56) References Cited

U.S. PATENT DOCUMENTS 5,550,373 A * 8/1996 Cole et al. ............... 250/338.1
5,909,280 A * 6/1999 Zavracky ................... 356/454
6,249,346 B1   6/2001 Chen et al.
6,295,130 B1   9/2001 Sun et al.
6,384,918 B1   5/2002 Hubble, III et al.
6,473,154 B2  10/2002 Tabata et al.
6,556,300 B2   4/2003 Tandon et al.
6,680,792 B2 * 1/2004 Miles ........................ 359/291

OTHER PUBLICATIONS

U.S. Appl. No. 10/833,231, filed Apr. 27, 2004, Mestha, et al.
U.S. Appl. No. 10/758,096, filed Jan. 16, 2004, Mestha, et al.
J. H. Correia, C. Couto, "MEMS: a New Joker in Microinstrumentation", *IEEE Industrial Electronics Society Newsletter*, Jan. 2000.

* cited by examiner

*Primary Examiner*—Patrick Connolly
(74) *Attorney, Agent, or Firm*—Fay Sharpe LLP

(57) ABSTRACT

Apparatus and methods are provided for implementing a full width array material scanning spectrophotometer by integrating a Fabry-Perot cavity filter with a silicon photodetector and a light focusing device (an optical guide or a SELFOC® lens). The material to be scanned is illuminated by a broad band illumination source (white LEDs or a fluorescence light source). The Fabry-Perot cavity gap can be tuned electromechanically to get multiple measurements to resolve the spectral distribution of the transmitted light signal. The array spectrophotometric architecture facilitates an elongated, substantially linear band detection and the associated spectral reconstruction technique resolves spectral distribution in the presence of multiple resonant peaks.

2 Claims, 6 Drawing Sheets

Wavelength for 0.2 micron gap

Wavelength for 0.35 micron gap

FULL WIDTH ARRAY MECHANICALLY TUNABLE SPECTROPHOTOMETER

Cross-reference is made to copending, commonly assigned applications, U.S. application Ser. No. 10/833,231, filed Apr. 27, 2004, by Lalit Keshav Mestha, et al., entitled "Full Width Array Scanning Spectrophotometer", (Attorney Docket No. A2517-US-NP) and U.S. application Ser. No. 10/758,096, filed Jan. 16, 2004, by Lalit Keshav Mestha, et al., entitled "Reference Database and Method for Determining Spectra Using Measurements From an LED Color Sensor, and Method of Partitioning a Reference Database" (Attorney Docket No. D/A2361), all of which are herein incorporated by reference.

BACKGROUND

The present embodiments relate to spectrophotometer scanning systems particularly suitable for high speed online document color analysis. They are also applicable to item identification and characterization in many non-graphic arts applications ranging from paint industry color measurements to biotechnology applications such as performing DNA profiling. The embodiments also relate to defining a wide range spectra (visible, UV, infrared) for a particular media using a selected set of measured samples set by a tunable optical filter.

Spectroscopy is the measurement and analysis of electromagnetic radiation absorbed, scattered, or emitted by atoms, molecules, or other chemical or physical materials. Each object affects light in its own unique way. When light waves strike an object, the object's surface absorbs some of the spectrum's energy, while other parts of the spectrum are reflected back from the object. The modified light that is reflected from the object has an entirely new composition of wavelengths. Different surfaces containing various pigments, dyes, and inks (or chemistry/materials) generate different but unique wavelength compositions. Light can be modified by striking a reflective object such as paper; or by passing through a transmissive object such as film or a transparency. The pattern of wavelengths that leaves an object is the object's spectral data, which is often called the "finger print" of the object. Measuring spectral content of the object can give its intrinsic properties. For example, the region of the electromagnetic spectrum visible to the human eye ranges from about 400 nm to 700 nm, and if spectral measurements can be made in that wavelength range, then one can determine "the color of the object". The amount of reflectance intensity decomposed at each wavelength is the most complete and infallible description of the color one can see. Hence in this case, the spectrophotometer becomes a true color sensor. If the UV-Vis spectrum (Ultraviolet and visible spectrum) is from 200 nm to 800 nm, then the UV-V spectrum could be used to identify the material composition—which is a form of non-contact, non-reactive chemical test—which can be used to analyze the compounds.

Spectrophotometers with a broad range of spectral synthesis have a wide range of application, including color printing, color measurements in displays, paints, textiles, electronic cameras, chemical analysis, environmental monitoring, measurement of bio-samples for medicine or personal identification, etc. All commercial spectrophotometers tend to be large in size with many optical elements.

Prior known full width array spectrophotometer systems utilized a linear array of photodetectors to detect an illuminated band of a test target, but required multiple different LED illumination sources of plural different color emissions in order to obtain an appropriate range of spectral response detections. In addition, such different color emissions had to be sequentially timed for emissive operation so the desired responses could be correspondingly distinguishably detected.

U.S. Pat. No. 6,295,130, issued Sep. 25, 2001, to Sun et al., entitled "Structure and Method for a Microelectromechanically Tunable Fabry-Perot Cavity Spectrophotometer", discloses a measurement system for spot measurements requiring a single peak, which is generally difficult to achieve in Fabry-Perot devices. By "MEMS" it is meant "Micro-Electro-Mechanical-Systems" and by "Fabry-Perot cavity" it is meant an optical interference filter having a parallel glass plate silvered on the inner surfaces so that the incoming wave-is multiply reflected between them and ultimately transmitted. (cf. "MEMS: a New Joker in Micro-instrumentation", J. H. Correia et al., *IEE Industrial Electronics Society Newsletter*, January 2000; and, commonly assigned U.S. Pat. No. 6,249,346, issued Jun. 19, 2001 and entitled, "Monolithic Spectrophotometer".)

Usually, scanner characterization is needed to transform scanned RGB values (scanner output signals) to colorimetric (i.e., visual) signals. Today's document scanners actually sense colors in terms of RGB coordinates, which approximate the human visual system. Most scanners are deviant from the human visual system in ways that differ depending on the media and ink being scanned. To address this problem, different characterizations, or profiles are built for different media. Creation of profiles for multiple material, media and image combinations results into loss of productivity. This can be easily fixed by having a wide area scanning spectrophotometer embedded on each printing device.

There is a need for an optical sensor that has the potential to measure colors at high printer speeds, at high resolution and with improved accuracy. A full width array optical sensing system, applicable for insitu measurements would provide significant advantages for automating publishing, production and decision processes in document production system via feedback through the proofing, prepress and creation stages. Such an optical sensor system would also have the capability for useful applicability for non-printing related applications, where materials or items can be identified through their color spectra.

BRIEF SUMMARY

A full width array document scanning spectrophotometer (FWAS) integrates a Fabry-Perot cavity filter with a silicon photodetector and a light focusing device, such as an optical fiber guide or a SELFOC® lens. An item or material such as a print document to be scanned for calibrating and ultimately maintaining color accuracy, is illuminated by a two-sided LED illuminator bar wherein the illuminator bar is advantageously comprised of white LEDs or a fluorescence light source. The thickness of the cavity filter can be tuned electrostatically with a switching circuit to give multiple transmissive frequency measurements to the photodetector and a sampling circuit for resolving the spectral distribution of the transmitted light signal from the object media. The architecture of the full width array spectrophotometer facilitates representative spectral detection without the need for plural different color light source emissions, thereby engendering multiple illuminate reflections from a single light source on a target media to produce multiple samples. Thus, multiple samples are derived from a single illuminate source by corresponding adjustment by the optical filter with enough samples in the Fabry-Perot cavity to define a characterizing spectral response. A spectral reconstruction technique facilitates the resolving of the spectral distribution in the presence of multiple resonant peaks transmitted by the filter.

More particularly, an elongated array of multiple, closely spaced photodetectors are disposed adjacent the illumination source wherein the spectrophotometers are positioned to receive light reflected from the target sample. The switching circuit selectively ramps a voltage source to the optical filter for microelectronically tuning the cavity filter and selectively transmitting therethrough the desired frequencies of reflected light which can be sampled by the sampling circuit for generating the desired representative spectral responses of the target sample.

Methods are provided for full width scanning color analysis of transversely extensive color test targets in a test target path, such as a color printer path, with a full width array spectrophotometer. A substantially linear elongated array of closely spaced multiple LED illumination sources are illuminated for illuminating a transversely substantial span of the test target with an illuminated band extending transversely across the test target. Reflected light from the illuminated band is detected with a full width array of multiple, closely spaced plural photodetectors disposed adjacent to and extending substantially parallel to the array of illumination sources. The photodetectors are positioned to receive light reflected from the illuminated band fully across the test target. The reflected light is selectively filtered with the full width array of tunable optical filters associated with the photodetectors for generating a detected spectra from the test targets representative of a color thereof. The optical filters preferably comprise microelectronically tunable Fabry-Perot optical filters which are adjusted by a switching circuit for transmitting selected frequencies of the reflected light from the test target to the photodetectors.

The disclosed systems and method may be operated and controlled by appropriate operation of conventional control systems. It is well known and preferable to program and execute such control functions and logic with software instructions for conventional or general purpose microprocessors, as taught by numerous prior patents and commercial products. Such programming or software may of course vary depending on the particular functions, software type, and microprocessor or other computer system utilized, but will be available to, or readily programmable without undue experimentation from, functional descriptions, such as those provided herein, in the cited prior patents and applications herein, and/or prior knowledge of functions which are conventional, together with general knowledge in the software or computer arts. Alternatively, the disclosed control systems or methods may be implemented partially or fully in hardware, using standard logic circuits or single chip VLSI designs.

The term "reproduction apparatus" or "printer" as used herein broadly encompasses various printers, copiers or multifunction machines or systems, xerographic or otherwise. The term "sheet" or "document" herein refers to a usually flimsy physical sheet of paper, plastic, or other suitable physical substrate for images, whether precut or web fed.

As to specific components of the subject apparatus or methods, or alternatives therefor, it will be appreciated that, as is normally the case, some such components are known per se in other apparatus or applications, which may be additionally or alternatively used herein, including those from art cited herein. For example, it will be appreciated by respective engineers and others that many of the particular components and component actuations or drive systems noted herein are merely exemplary, and that the same novel functions can be provided by many other known or readily available alternatives. All cited references, and their references, are incorporated by reference herein where appropriate for teachings of additional or alternative details, features, and/or technical background. What is well known to those skilled in the art need not be described herein.

DRAWING DESCRIPTIONS

DETAILED DESCRIPTION

Figure 1:
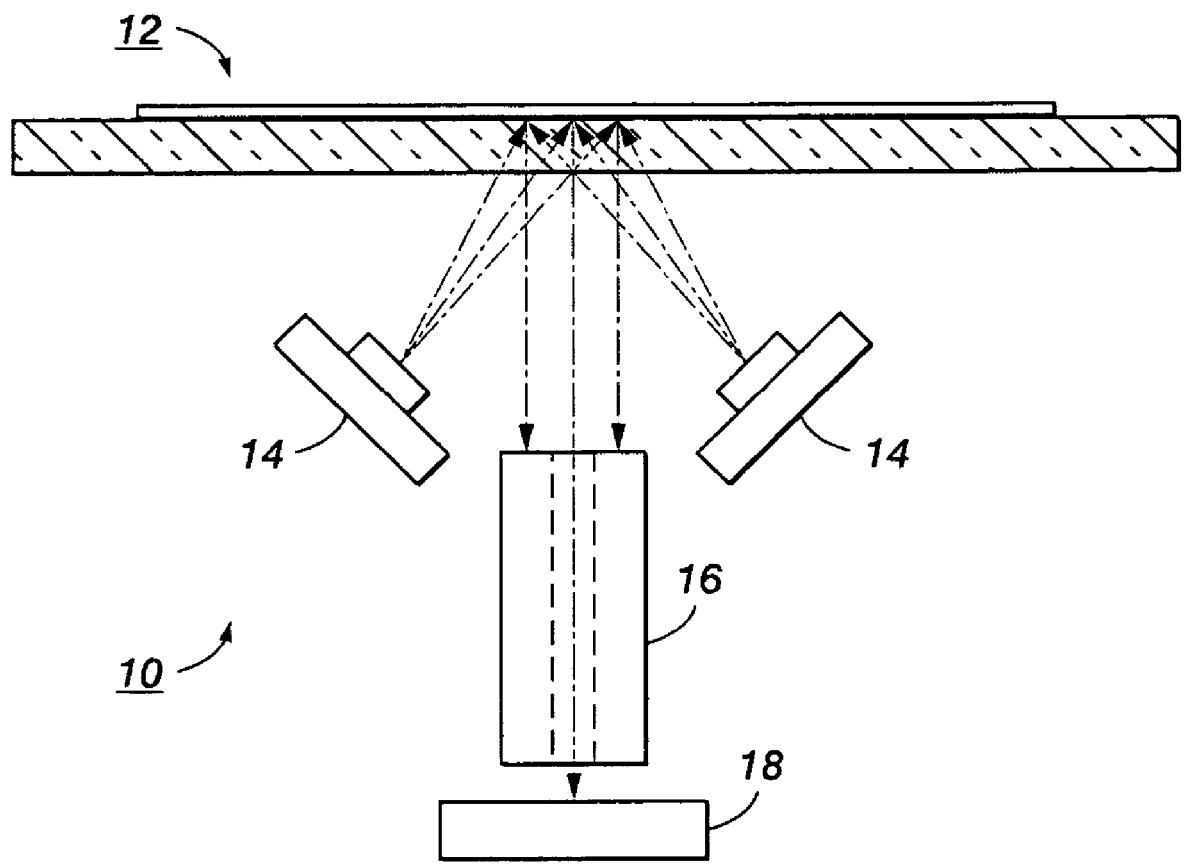
FIG. 1 is schematic side view of one example of the subject full width array scanning spectrophotometer system, shown scanning a printed sheet in the output path of a xerographic printer.

Describing now in detail the exemplary embodiments with reference to the Figures, they illustrate a full width array mechanically tunable Fabry-Perot spectrophotometer system 10. By "full width" is meant a document width, but is intended to also include an array having more than one spectrophotometer in a tightly integrated fashion. By "Fabry-Perot" is meant not only conventionally known Fabry-Perot interferometers, but also a wide range of all kinds of adjustable optical filters, and in particular, for example, a Bragg mirror dielectric stack Fabry-Perot interferometer. With particular reference to FIG. 1, a document or material item is to be scanned 12 for purposes of assessing color accuracy, e.g., a printer feedback control system, or for identification of a nature or color aspect of the target material, e.g. a substrate, paint color, biosamples, etc. The system assembly comprises sources of illumination 14 preferably comprising a two-sided LED illuminator bar, and in this embodiment advantageously instrumented with white LEDs, or could be a fluorescence light source of the kind used in three or four-row full width array image sensors. Alternatively, a full width array illumination can be provided by the user with intermediate shaped plastic light guides splitting or spreading the light from a light source at the edge of the full width illuminator, such as is disclosed in U.S. Pat. No. 6,473,154 for a document scanner. The entire imaging module assembly comprises the illuminators 14, a light focusing device assembly 16 such as a SELFOC®, a lens or optical fiber assembly and a spectral photometric sensor assembly 18. In operation, the sensor assembly 18 could be stationary and the document could be moved over it using constant velocity transport, or the document could be stationary and the spectral photometer module could be moved at a constant velocity, as in done in platen scanners. The SELFOC® lens or alternative optical fiber assembly 16 can be built to focus light from each pixel from the document 12 to the array 18, preferably comprising a plurality of MEMS sensors. Alternatively, a plurality of photodetectors (photodiodes) can be associated with a single light focusing device where higher resolutions or enhanced processing efficiencies are desired.

The basic structure and operational methods for a micro-electromechnically tunable Fabry-Perot cavity spectrophotometer are described in detail in aforementioned U.S. Pat. No. 6,295,130, and which descriptions is herein incorporated by reference.

Figure 2:
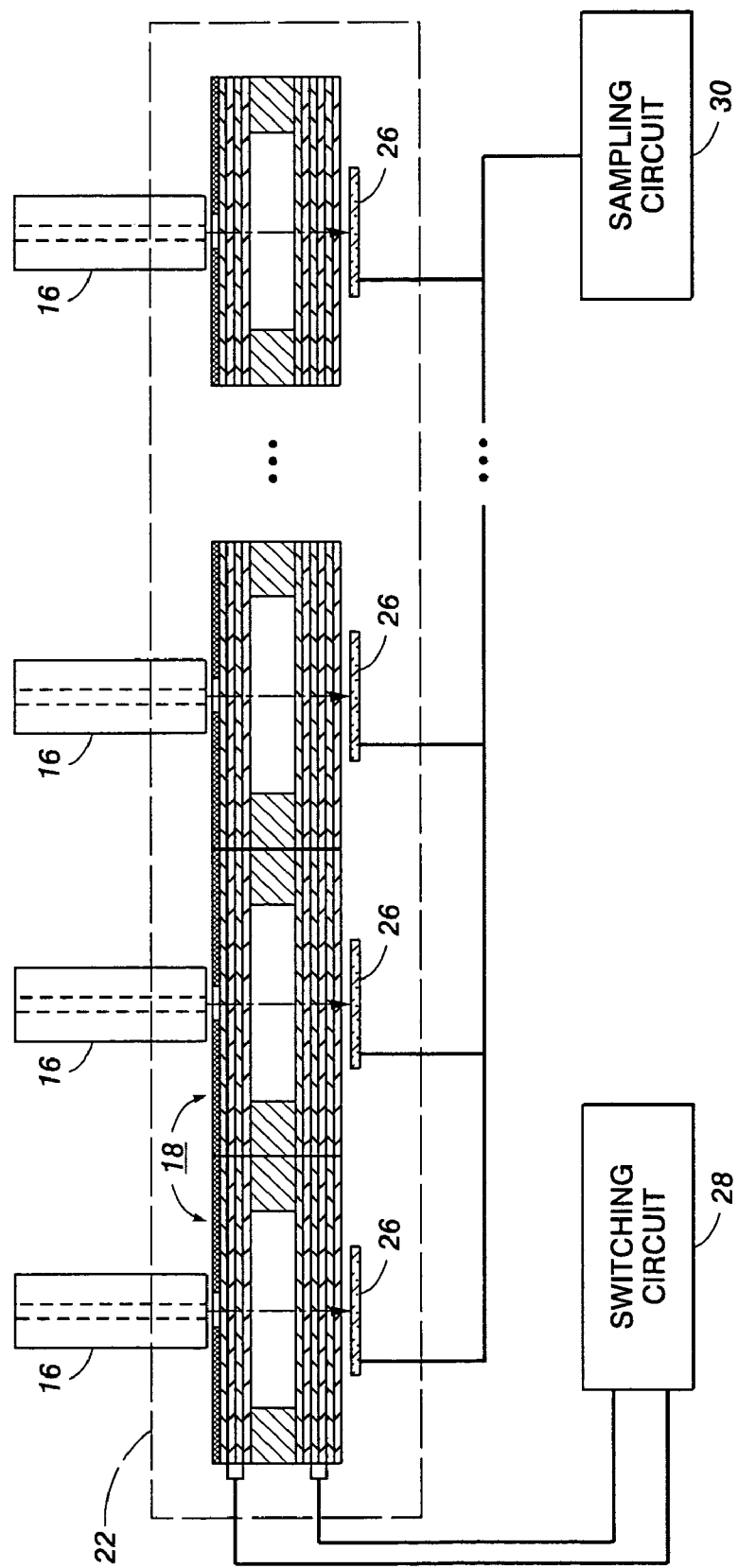
FIG. 2 is an elevated side view of a full width array assembly with spectrophotometers, particularly illustrating the Fabry-Perot cavity construction in combination with schematic representations of associated control systems.

FIG. 2 illustrates the arrayed assembly architecture of the MEMS full width array sensor assembly 22. Reflected light from the document 12 is communicated through the light focusing device assembly 16 (e.g., an optical fiber) through the optical filter 18 to the photodetectors 26. As is well known in the art and is discussed in the aforementioned '130 patent, the Fabry-Perot cavity thickness can be tuned electrostatically by switching circuit 28 (using drive circuits shown in the '130 patent) to get multiple measurements to resolve the spectral distribution of the transmitted light signal. The gap length of the cavity in the filter is related to the tunable voltage from the switching circuit 28 and provides either a single or multiple peak of transmitted frequency of the reflected light.

FIGS. 4(a)-4(e) illustrate a typical transmission spectra of such a device 18 for various gap lengths. Since there are multiple peaks, resolving spectral distribution of the transmitted light requires processing.

For scanning a document with 600 dots per inch, 8.5×11 square inch, the scanning area (33.66 million pixels) requires about 5400 Fabry-Perot cavity sensors (assumes 42 um width for each Fabry-Perot sensor). Using known electronics and photodetector assemblies a scanning speed of 30 to 50 microseconds per scan line can be achieved. This amounts to a capability of around 200 to 500 pages per minute scanning speed.

The external diameter of the optical fiber is the limiting factor in the measurement aperture for full width scanning applications when external fiber is used to guide the reflected light to the detector array. With known optical fiber technology, the unit can be assembled to contain about 40 um of external diameter (about 10 um internal diameter) for each sensor. In a single die of 1.5 cm×2 cm, around 150,000 sensors (300×500) can be assembled.

Figure 3:
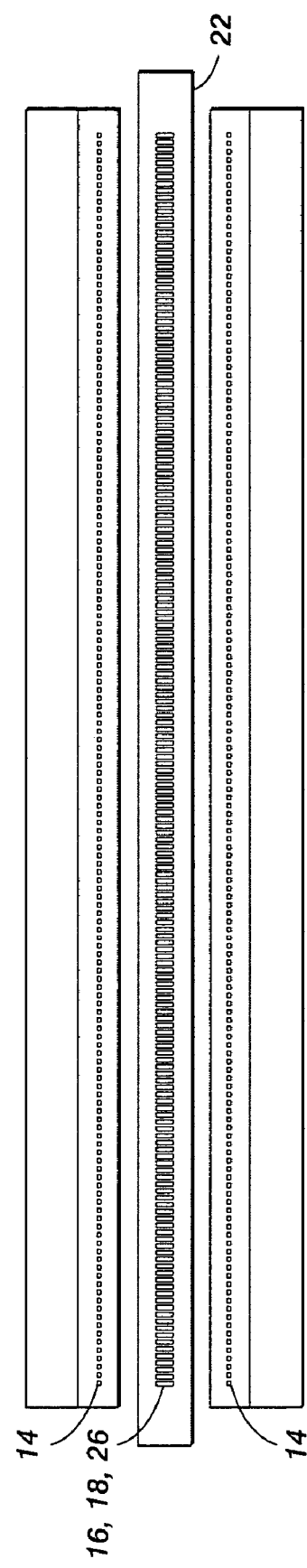
FIG. 3 is a top view of the full width array scanning spectrophotometer particularly illustrating the arrayed assembly, and without input sheet or other color test object present.
Figure 4A:
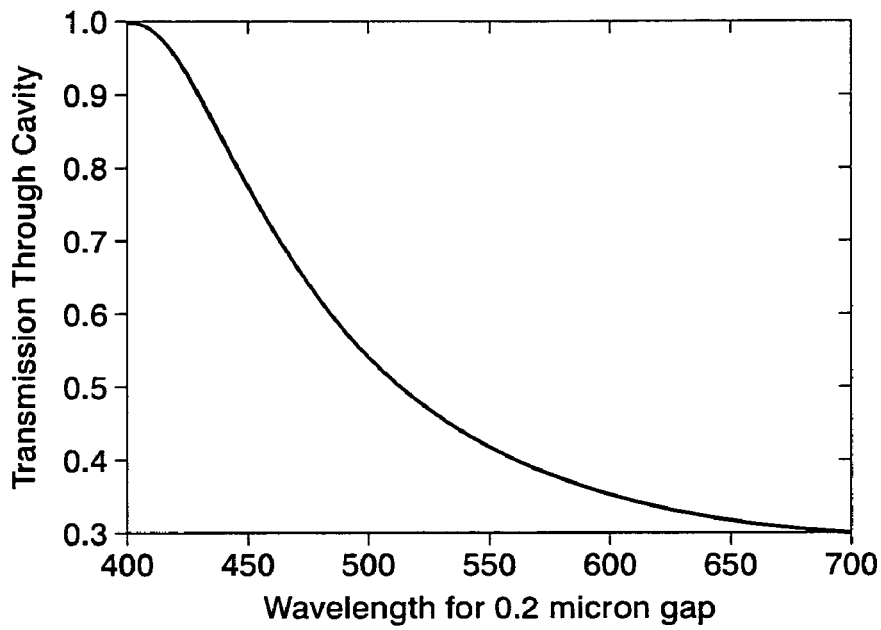
FIGS. 4(a)-(e) are schematic illustrations of selected transmission spectra of an optical filter embodiment corresponding to differently tuned cavity gaps.
Figure 4B:
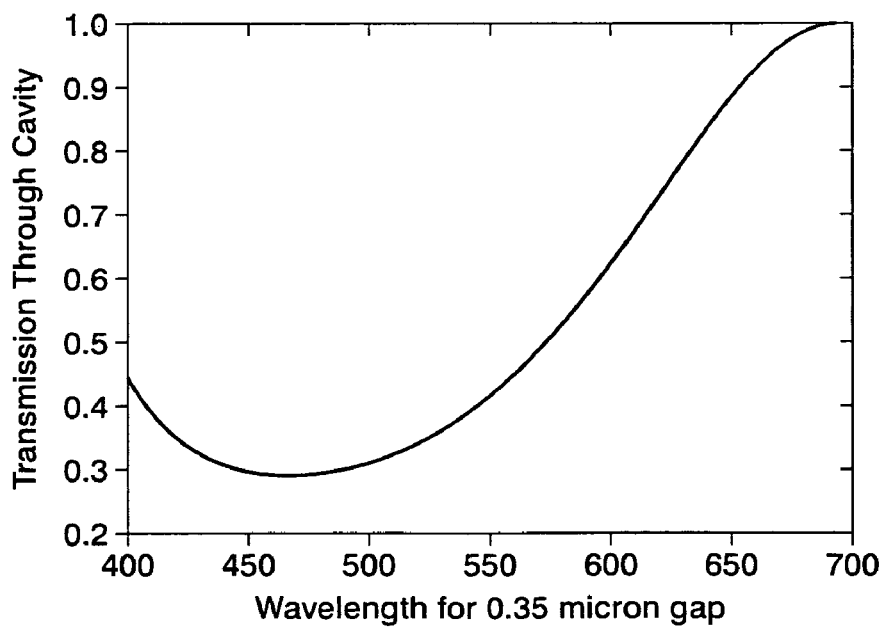
Figure 4C:
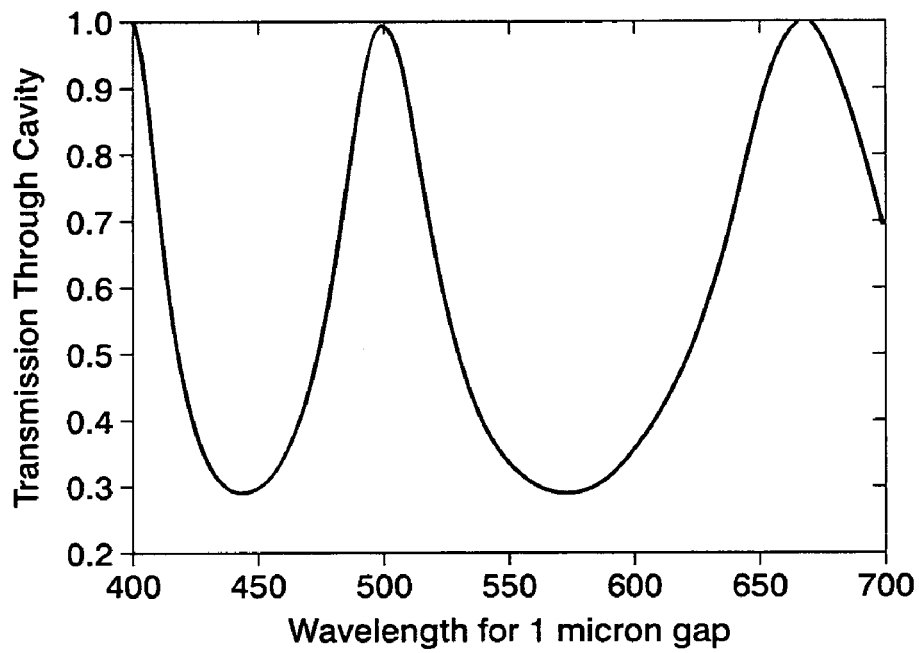
Figure 4D:
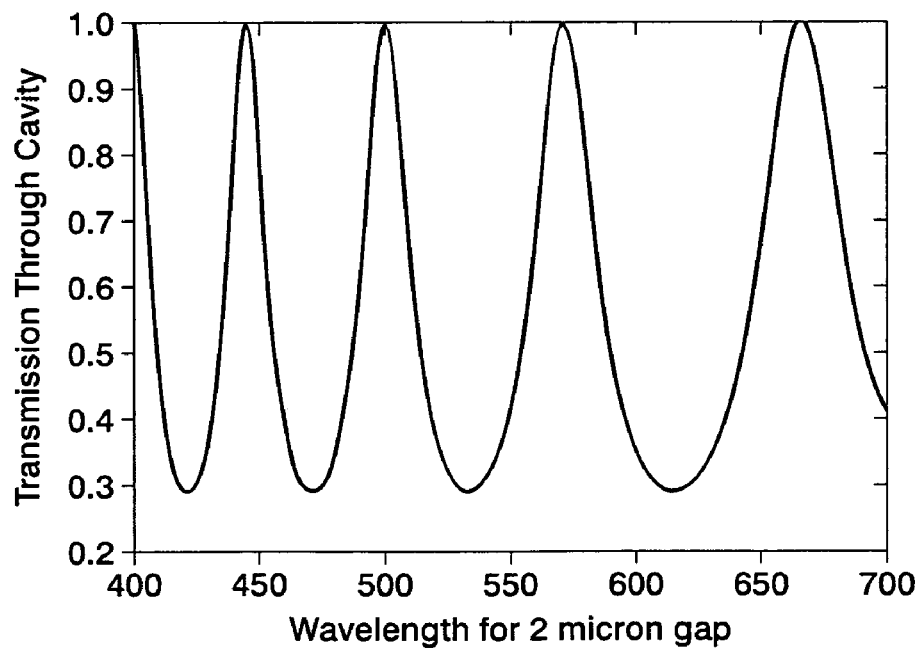
Figure 4E:
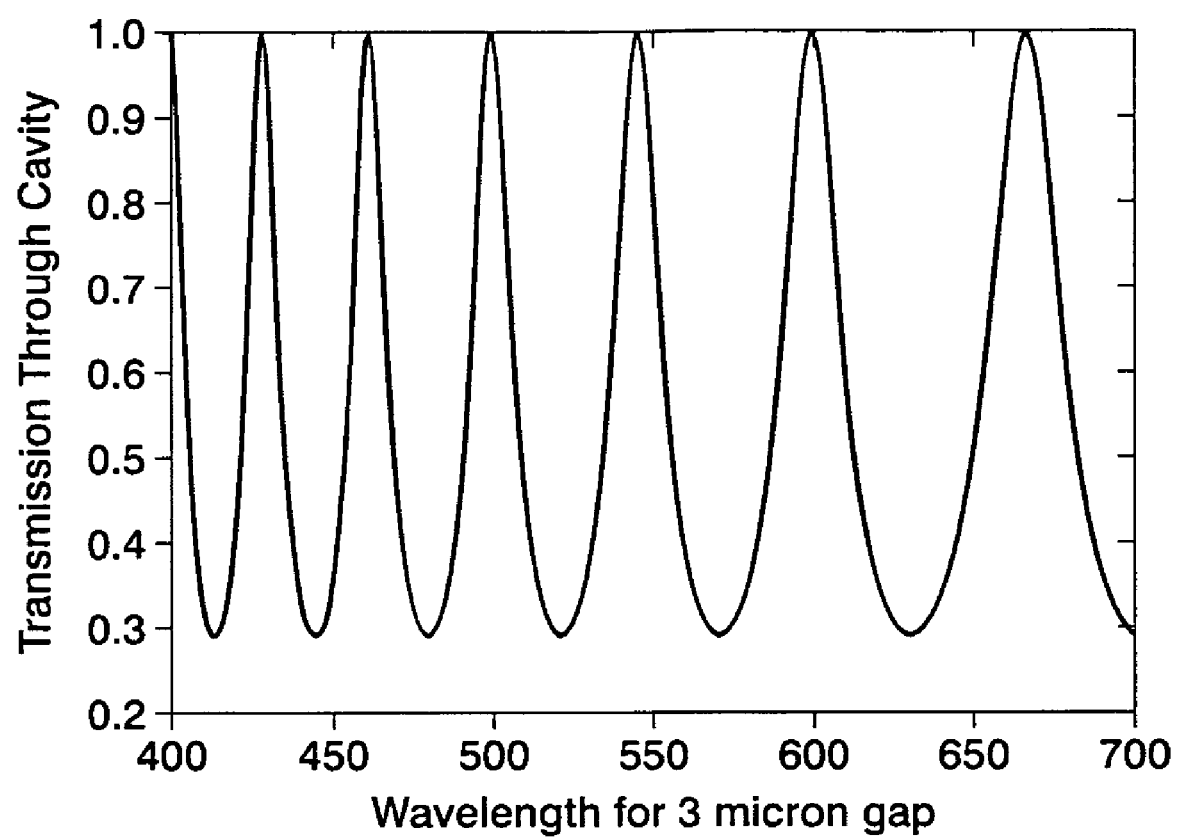

With reference to FIG. 3, the illuminated spectrophotometric assembly 22 includes a substantially linear elongated array of closely spaced filter 18 and photodetector 26 assemblies adjacent linear elongated arrays of closely spaced multiple LED illumination sources 14 disposed to transversely span a test target path to illuminate a transverse illuminated band of the color test targets. The photodetectors are just disposed adjacent to and extend substantially parallel to the array of illumination sources so that the illuminated bar assembly 22 can receive light reflected from the illuminated band of the test target.

It is generally difficult to optimize Fabry-Perot device parameters to get a single peak sweeping between the light wavelengths of interest. Accordingly, the subject embodiment includes an algorithm for extracting the full visible spectra from a single or multiple-peak Fabry-Perot cavity filter.

If $V_{gi}$ is the measure of the amount of light flux at the output of the detector circuitry, then the simplest first order linear model (this ignores the effects due to scattering, illumination geometry, etc.) of the sensing system for a single switching event can be written as follows:

$$V_{gi} = \sum_{K=0}^{k=N} S(\lambda_k) R(\lambda_k) T_{gi}(\lambda_k) \quad (1)$$

Where $R(\lambda_k)$ is the reflectance spectra of the material, $V_{gi}$ is the integrated output of the detector for wavelengths $\lambda_k$, k=0, 1, . . . N, $S(\lambda_k)$ is the illuminant spectra and $T_{gi}(\lambda_k)$ is the transmission spectra at wavelength $\lambda_k$ for a gap size $gi_i$. N is the total number of wavelength samples used for integrating the reflected power spectra from the device. Note that the transmission spectra contain the photodetector spectra of the device and $gi_i$ is used to denote the gap setting.

If the gap is varied between minimum to maximum in some known steps, say g1, g2 . . . , gN, then, the following matrix equation can be written:

$$V = DR \quad (2)$$

Where the signal vector V, reflectance vector R and detector matrix D are expressed as follows:

$$\underline{V} = \begin{bmatrix} V_{g1} \\ V_{g2} \\ . \\ . \\ V_{gN} \end{bmatrix}; \underline{R} = \begin{bmatrix} R(\lambda_1) \\ R(\lambda_2) \\ . \\ . \\ R(\lambda_N) \end{bmatrix} \text{ and } \underline{D} = \quad (3)$$

$$\begin{bmatrix} S(\lambda_1)T_{g1}(\lambda_1) & S(\lambda_2)T_{g1}(\lambda_2) & . & . & S(\lambda_N)T_{g1}(\lambda_N) \\ S(\lambda_1)T_{g2}(\lambda_1) & S(\lambda_2)T_{g2}(\lambda_2) & . & . & S(\lambda_N)T_{g2}(\lambda_N) \\ . & . & . & . & . \\ . & . & . & . & . \\ S(\lambda_1)T_{gN}(\lambda_1) & S(\lambda_2)T_{gN}(\lambda_2) & . & . & S(\lambda_N)T_{gN}(\lambda_N) \end{bmatrix}$$

From Equation (2), if the processing matrix is known and is invertible, then the reflectance spectra for any sample can be obtained using the following equation:

$$R = D^{-1} V \quad (4)$$

Equation 4 shows how to compute the reflectance spectra using the inverse of the detector matrix. The processing matrix is precalculated and stored in the sensor processor in the sampling circuit 30. The processing matrix is invertible, when all the columns of the matrix are linearly independent, and this is the case when the peaks occur at different wavelengths per gap. If the Fabry-Perot device is tuned to a single peak, then the detector matrix is diagonal.

This method of spectral reconstruction does not require any pre-characterization of the sensor output with respect to a reference sensor as is done in known LED/Image sensor devices. A full ramping of the gap voltage (as in a saw tooth wave) per scan can give an equivalent change in the gap. For example, sampling of the photo-detector signal 31 times during the ramp per scan gives a vector V per pixel by the precalculated matrix as in Equation 4. With such a processing method, this device can now generate true spectra for each pixel and has the potential for tuning to any wavelength of interest beyond the visible range within the scope of the Fabry-Perot device.

The scaling factor or an offset may be required in Equation 1 (not shown) and is extracted using the sensor output for the reference surface or by using the training samples and various known signal processing methods. It can be done every time the sensor calibration is done with a reference surface, such as a white calibration surface.

If the errors in the detector matrix of Equation 4 are zero, then the spectral measurements contain no errors. For color applications, generally 10 nano meter spectral resolution between 400 nm to 700 nm is desirable. For such applications, the detector matrix will be of size 31×31 elements, calculated offline using transmission and the illumination spectra. However, if the desire is to expand the sensor resolution and range based on requirements for much wider applications, then a suitable matrix size is chosen. For example, if the desired spectra is required at a resolution of 1 nano-meter wavelength between 400 nm to 700 nm, then the detector matrix will have a size of 300×300 elements. The detector signal has to be sampled 300 times for every scanning operation.

Since generally there are errors in the detector matrix (may be due to fluctuations in the gap voltage or noise in the illumination spectra) the expected accuracy can be simulated from the device for a small range of tunable voltages. Hence, better control of the voltage source, illumination and improved signal to noise ratio inferred through simulation can give us potentially very accurate spectral measurements.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications, variations, improvements, and substantial equivalents.

The invention claimed is:

1. A method of full transverse scanning color analysis of color printed sheets moving in a color printer path with a full width array spectrophotometer, comprising:

illuminating at least one substantially linear elongated array of broad band illumination sources extending sufficiently in a substantially linear dimension to transversely substantially span said color printer path to illuminate the printed sheets with a broad band transverse illumination source extending transversely across said color printed sheets moving in said color printer path, detecting reflected light from said illumination source and a corresponding portion of the printed sheets with a full width array of tunable spectrophotometers being positioned to receive light reflected from said transverse illumination source fully across said print media sheet moving in said paper path;

selectively filtering the reflected light with a full width array of tunable optical filters associated with photodetectors for generating a detected spectra from the corresponding portion of the printed sheets representative of a color thereof including multiple transmission frequencies corresponding to multiple detected samples for the detecting; and, resolving the detected spectra with a sampling circuit for effecting the color analysis wherein multiple illuminate reflections from the corresponding portion of the printed sheets generate the detected spectra from the broad band illumination sources.

2. The method of claim 1 wherein the illuminating utilizes a white LED or a fluorescent light source.

* * * * *